(12) United States Patent
Nowak et al.

(10) Patent No.: US 6,861,052 B1
(45) Date of Patent: Mar. 1, 2005

(54) SEPARATION PROCESS

(75) Inventors: Götz Nowak, Erfurt (DE); Elke Bucha, Erfurt (DE)

(73) Assignee: HaemoSys GmbH, Jena (DE)

( * ) Notice: Subject to any disclaimer, the term of this patent is extended or adjusted under 35 U.S.C. 154(b) by 0 days.

(21) Appl. No.: 09/517,863

(22) Filed: Mar. 3, 2000

(30) Foreign Application Priority Data

Mar. 4, 1999 (DE) .......................................... 199 09 584

(51) Int. Cl.[7] .......................... A61K 31/74; A61K 9/14; A61K 9/16

(52) U.S. Cl. ..................................... 424/78.08; 424/489

(58) Field of Search ............................. 424/78.08, 489, 424/490, 497, 501, 484, 486, 487

(56) References Cited

U.S. PATENT DOCUMENTS 4,642,335 A * 2/1987 Miyashiro et al. .......... 530/409
5,736,625 A * 4/1998 Callstrom et al. .......... 530/402

* cited by examiner

*Primary Examiner*—James M. Spear
(74) *Attorney, Agent, or Firm*—Akin Gump Strauss Hauer & Feld, LLP

(57) ABSTRACT

The present invention relates to a process for separating substances, which are bonded to a polymer surface via a linker, by adding a polar organic solvent.

16 Claims, 2 Drawing Sheets

PEG hirudin separation by rinsing for 10 minutes with methanol solutions of various concentrations
-PEG hirudin recovery in the rinsing solution-

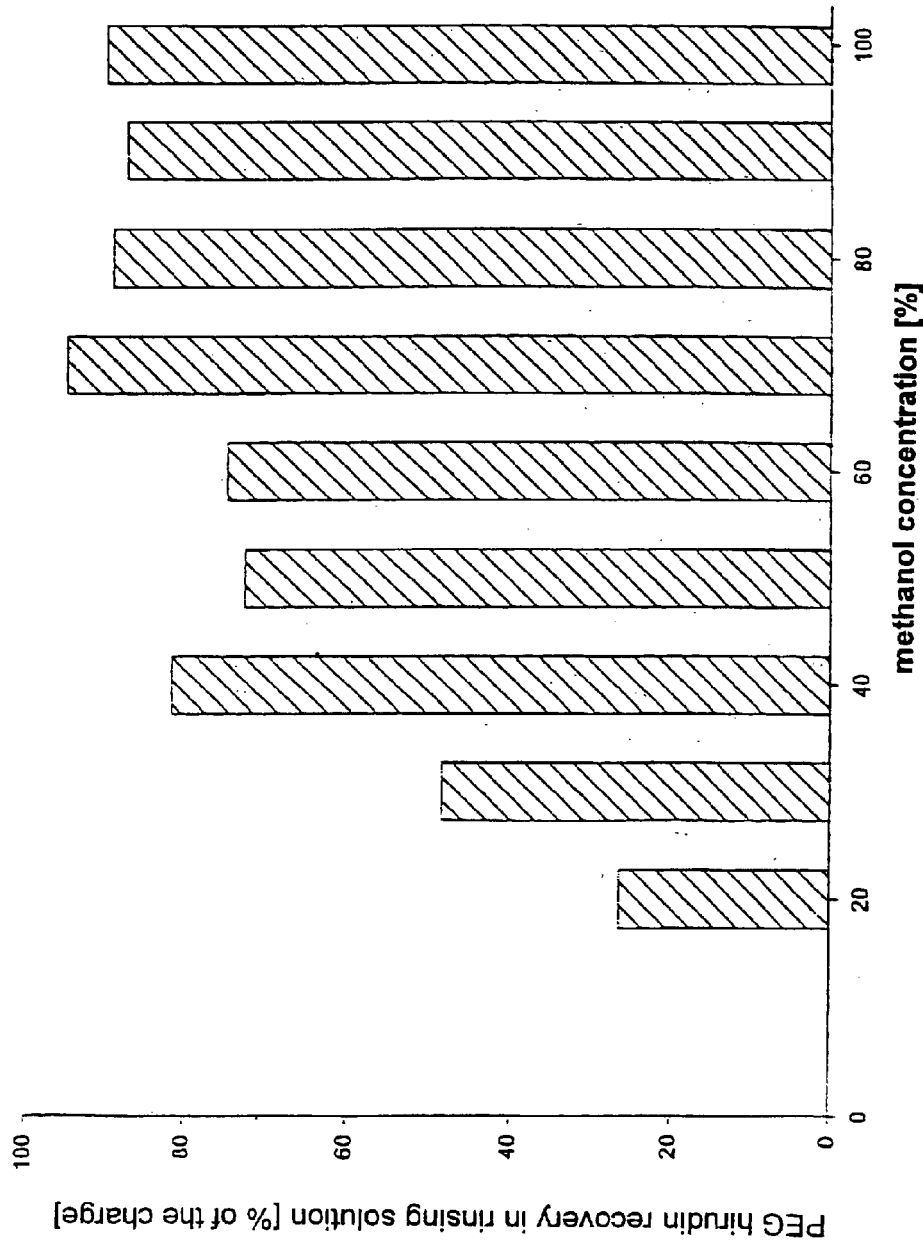
Fig. 1: PEG hirudin separation by rinsing for 10 minutes with methanol solutions of various concentrations
-PEG hirudin recovery in the rinsing solution-

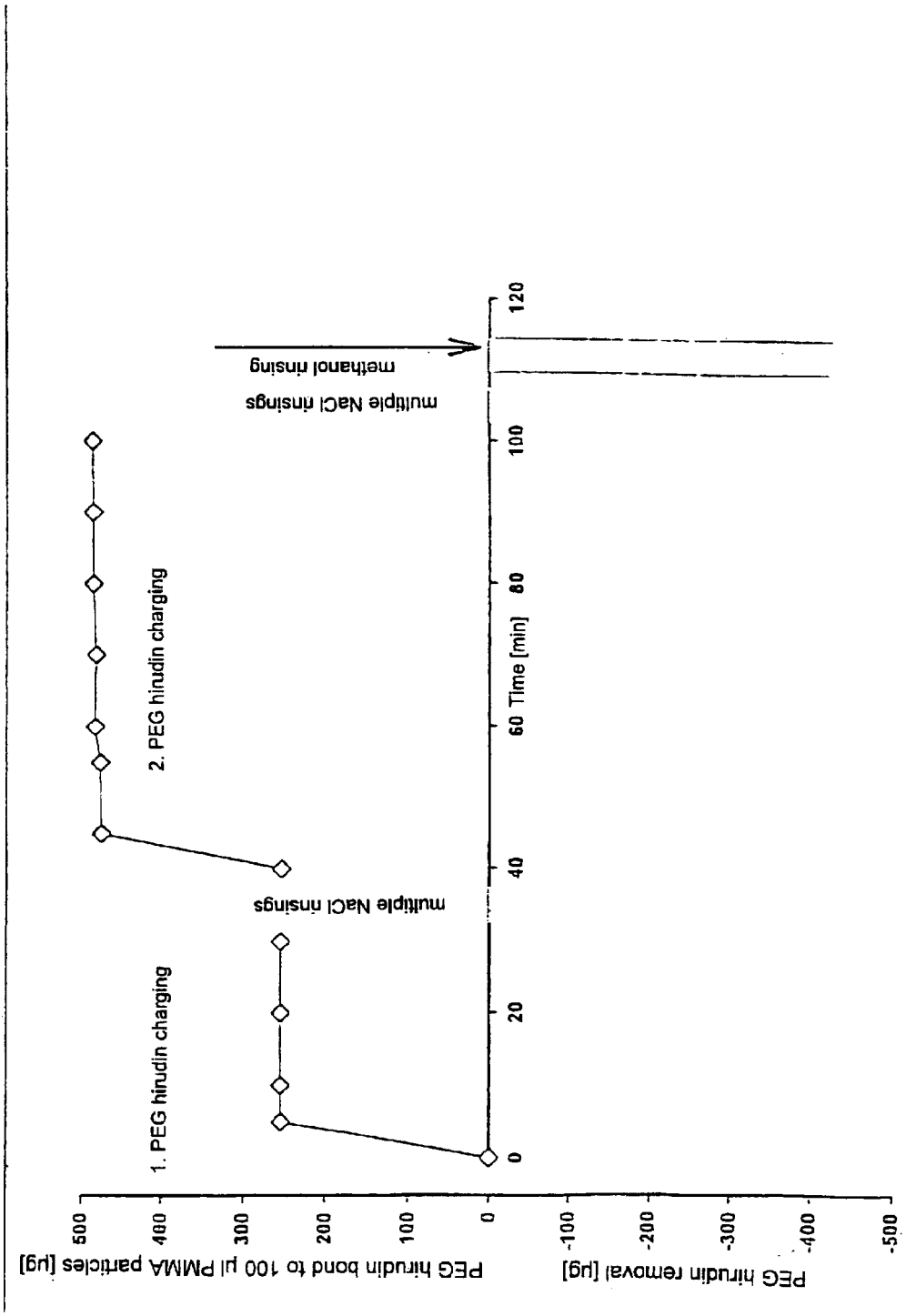
Fig. 2: Reusability of PEG hirudin and PMMA particles after separation of the PEG-PMMA bond by methanol rinsing

SEPARATION PROCESS

BACKGROUND OF THE INVENTION

1. Field of the Invention

The present invention relates to a process for separating linker-coupled substances from a polymer surface, wherein the bond between the linker and the surface is separated by one or several polar organic solvents, with the linkers according to the present invention comprising at least one structural element capable of forming a hydrogen bond. Polymers on the surface of which the bond to be separated according to the invention occurs, comprise, preferably in side chains of the polymer backbone, carbonyl groups in the form of keto groups or carboxylic acid groups or their derivatives.

2. Description of the Related Art

The principle of interaction of certain linkers with such polymer surfaces is described in WO 98/46648. By using linker-modified surfaces and/or linker-modified active substances, this principle can be employed for example to remove active substances from liquids or to expose such substances to liquids. The cited application furthermore discloses the use of the interaction principle in connection with comprehensive medical processes. Thus, by means of an adsorption system consisting of a polymer surface and a linker being coupled therewith and comprising functional groups, active substances which form a bond with the functional groups present in the linker can be removed from body liquids. Moreover, such a system allows the selective introduction of active substances into the body of a patient without the substance spreading widely in the body, which otherwise might cause potential complications and side effects. Also, the coupling principle described in the application WO 98/46648 allows a modification of surfaces getting into contact with physiological systems such as for example prostheses, filters for physiological liquids or dialysers. The linkers, comprising at least one structural element capable of forming a hydrogen bond, show a surprisingly high bond strength after being applied to said surfaces so that they can be removed from these surfaces neither by increasing the temperature, e.g. to up to 70° C. nor by rinsing with aqueous solutions, even if the solutions had high ionic strengths such as 2N glycine or 2N urea, or pH values in the range from 2 to 13.

In certain applications, however, the possibility of a gentle removal of the linker-coupled substances from the surface matrix would be desirable. This is the case for example if an analysis of the substances after their coupling with the linker and the removal from the respective liquid for diagnostic or research purposes is desired. Moreover, a separation would be necessary in cases wherein before reusing the surface or the linker-coupled substance, either one or both components can be sterilized in order to be then reused separately or in combination.

SUMMARY OF THE INVENTION

Thus the object of the present invention is to provide a gentle, non-destructive yet simple and inexpensive process for the separation of a system comprising a surface and substances coupled therewith by means of linkers, in order to ensure the reusability of all components. According to the invention this object is solved by subjecting the system to a polar organic solvent. Surprisingly it was found that such solvents, even in the form of aqueous solutions at low concentration, are capable of completely separating the bond between the linker-coupled substance and the polymer surface. Both the substances and the surface retain their functional ability after separation of the bond.

BRIEF DESCRIPTION OF THE SEVERAL VIEWS OF THE DRAWINGS

For a further understanding of the nature, objects and advantages of the present invention, reference should be made to the detailed description, read in conjunction with the following figures, wherein:

FIG. 1 is a graphical representation of the data in Table 1 showing the percent PEG recovery versus methanol concentration of a rinsing solution; and FIG. 2 is a graphical representation showing the reusability of purified PMMA particles and recovered PEG hirudin.

DETAILED DESCRIPTION OF INVENTION

Polymers, from which linkers together with substances coupled therewith can be separated according to the process of the present invention, are described for example in WO 98/46648. Homopolymers or copolymers are employed, in the preparation of which at least one monomer type is used containing, in addition to a polymerizable double bond or a polycondensable functional group, a further carbonyl group in the form of a ketone or a carboxylic acid or its derivative, said group not taking part in the polymerization reaction. Preferably, the polymer contains a structural element of the formula (A):

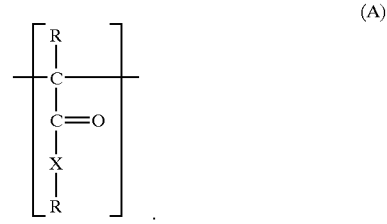

(A)

wherein the groups R can be the same or different and represent an alkyl or aryl group or a hydrogen atom. The alkyl group can be linear or branched and preferably has 1 to 20 carbon atoms. The aryl group preferably consists of 6 to 18, more preferably of 6 to 12 carbon atoms. The group X is facultative and represents O, N or $CH_2$. If X=N, N has another group R in addition to that given in formula (A), said group being defined independently of the other groups R as above.

As alkyl group, a straight-chain or branched, optionally substituted $C_{1-8}$ alkyl group is particularly preferred, for example a methyl, ethyl or propyl group. Examples of optionally present substituents comprise one or several halogen atoms, for example fluoro, chloro, bromo or iodine atoms or hydroxyl groups, $C_{1-6}$-alkyl or $C_{1-6}$-alkoxy or $C_{1-6}$-alkylthiol groups. As aryl group, a monocyclic or bicyclic, optionally substituted aryl group is particularly preferred, which optionally comprises one or several heteroatoms. Examples of such aryl groups are phenyl, 1- or 2-naphthyl, indenyl or isoindenyl groups. Examples of aryl groups containing a heteroatom are $C_{3-9}$-heteroaryl groups containing heteroatoms selected from oxygen, sulfur or nitrogen atoms. Monocyclic heteroaryl groups comprise for example pyrolyl, furyl, thienyl, imidazolyl, N-methylimidazolyl, N-ethylimidazolyl, benzothiazolyl, chinazolinyl, naphthylpyridinyl, quinolinyl, isoquinolinyl and tetrazolyl groups.

A preferred polymer containing such groups is polyalkylmethacrylate (PAMA) such as polymethylmethacrylate (PMMA), polyethylmethacrylate (PEMA) or polypropylmeth-acrylate. Particularly preferred from this group is the use of polymethylmethacrylate. Furthermore, polyvinylacetate, polycyclohexylmethacrylate or polyphenylmethacrylate can be used. Moreover, copolymers of the above-mentioned polymers in combination and/or together with one or several further polymer components, for example polystyrene, polyacrylnitrile or polyamides can be used. The ratio of the components in these copolymers is not particularly limited. Preferably, the portion of the carbonyl-functional monomers, e.g. alkylmethacrylate in such copolymers is at least 20 mol-%, more preferably 40 mol-%, and most preferably 60 mol-%.

The form of the polymer surfaces employed is not restricted by the principle of the present invention. For example, polymers in the form of films, hollow articles such as hoses, membranes or microparticles can be used.

Substances that are coupled with the polymer surface via a linker prior to the separation of the respective bond, can be selected depending on the application of the system. Preferably, pharmacologically or physiologically active substances are used. Examples are proteins, nucleic acids and cellular signal substances. Particularly preferred as protein is an enzyme, an antigen, an antibody, a tumor marker, a surface antigen, a ligand, a receptor, a surface active cell fragment of bacteria or viruses, or an immune messenger substance. The pharmacologically active substance is, for example, an anticoagulant, a metabolically active enzyme or a synthetic medicament such as an antibiotic, an anti-tumor agent or an enzyme inhibitor. Substances that may be used in the present system are described in detail in WO 98/46648.

Linkers, the bond to a specific polymer surface of which can be separated by the process disclosed, are molecules comprising at least two functional groups L1 and L2. One of these functional groups (L1) has to be capable of forming hydrogen bonds, thus enabling the linker to be bonded to the polymer surface. The functional group L2 is selected such that a bond between the linker and the substance to be coupled can be achieved. In order to apply several substances on the polymer surface at the same time, the simultaneous use of several linkers having different L2 groups is possible. However, there is also the possibility of using linkers of the same type having several L2 groups which are the same or different. Likewise, linkers can be used having several identical or different L1 groups. Preferably, L1 and L2 are connected via an alkyl chain or a polyether with 1 to 20 carbon atoms.

Preferably, the structural element L1 is a polar hydrocarbon atom as present for example in OH—, SH—, NH— or PH-bonds. This structural element is preferably present in a sufficiently water-soluble compound as linker, further carrying the structural element L2. —Particularly preferred is L1 being terminally bonded to the linker.

The functional group by means of which the substance can be bonded to the linker (L2) is for example a succinimidyl succinate, succinimidyl propionate, nitrophenylcarbonate, trisylate, epoxide, aldehyde, isocyanate or a maleinimide.

Functional groups L2, by means of which the preferred linkers can be modified for bonding an active substance, are described for example in the catalog of the company Shearwater Polymers, Inc., 2307 Spring Branch Rd., Huntsville, Ala. 35801 (USA).

As linkers, polyalkylenglycols are preferably used, particularly preferred is polyethyleneglycol (PEG). Furthermore, polyalkyleneimines, polyalkyleneamines or polyalkylenesulfides as well as polyoxazilines are preferred. Particularly preferred is the use of polyethylenglycols. The compounds mentioned preferably have a molecular weight of 5–50 kDa.

Polar organic solvents according to the present invention are solvents the molecules of which comprise a polar covalent bond which imparts to the molecule an electric dipole moment. The solvent molecules of the solvents to be used according to the invention preferably have an electric dipole moment in the gaseous phase which is greater than 1.0 D, more preferably greater than 1.4 D and most preferably greater than 1.6 D.

Preferably, organic compounds are used having polar oxygen groups such as alkanols and esters. Preferably, alkanols are used carrying up to 3 carbon atoms and up to 3 hydroxyl groups. Particularly preferred is methanol.

The organic solvents are preferably used in the form of an aqueous solution, the solvent concentration of which is preferably lower than 70% by volume and more preferably between 10 and 50% by volume.

Optionally, the solvent is to be selected depending on the substance bonded to the linker such that no irreversible reaction of the substance with the solvent can take place.

The separation of the linker-coupled substance from the surface can take place either by incubation of the linker-carrying surface in the solvent, by rinsing the surface, or by means of a through-flow method.

The invention will be illustrated on the basis of the following example:

EXAMPLE

Separation of the Peg Hirudin Bond to Polymethylmethacrylate (PMMA) Particles

Porous PMMA particles are charged with PEG hirudin in two batches. Subsequently a 10-minute rinsing process is carried out either using a methanol solution at different concentrations or, in comparative tests, using physiological salt solution (NaCl). The rinsing solutions are tested for separated PEG hirudin via a biological detection of the hirudin function and are then recovered.

After the rinsing of the particles, their loading capacity is tested by recharging with PEG hirudin solutions. The PEG hirudin recovered from the methanol rinsing solutions is also tested for its bonding capacity with PMMA particles.

By means of dilutions with a methanol concentration of up to 40%, more than 80% of the surface-bound PEG hirudin can be separated and recovered during only 10 minutes of rinsing (Tab. 1; FIG. 1).

The reusability of both purified particles and recovered PEG hirudin is demonstrated in FIG. 2. 50.5 million unused or purified particles, respectively, showed almost the same bond capacity for PEG hirudin. Further illustrated are the identical bonding characteristics of unused PEG hirudin and PEG hirudin which was recovered from methanol rinsing solution.

In all tests, the surface-fixed PEG hirudin was functionally active, which was demonstrated by the examination of the thrombin inhibition capacity.

TABLE 1

| Methanol concentration [%] | PEG hirudin coupled to PMMA particles [μg] | PEG hirudin recovered from methanol rinsing solution [μg] |
|---|---|---|
| 99.9 | 485.0 | 436.2 |
| 90 | 464.5 | 399.4 |
| 80 | 457.5 | 438.0 |
| 70 | 491.4 | 468.3 |
| 60 | 530.2 | 397.0 |
| 50 | 511.6 | 371.3 |
| 40 | 527.0 | 430.3 |
| 30 | 538.2 | 261.0 |
| 20 | 509.8 | 135.0 |
| 0 | 477.4 | In NaCl rinsing solution: 0.9 μg |

What is claimed is:

1. A process for separating a substance, which is bonded to a polymer surface via a linker, from said surface, the polymer surface comprising carbonyl groups and the linker having at least one functional group that forms a bond with a carbonyl group of the polymer surface, characterized in that the bond between the linker and the surface is separated by adding a polar organic solvent.

2. The process according to claim 1, wherein the solvent used is in the form of an aqueous solution in a concentration of not more than 70% by volume.

3. The process according to claim 1, wherein the polymer surface comprises at least one structural element having the formula

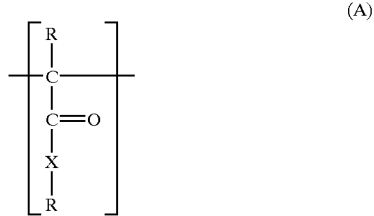

(A)

wherein X is $CH_2$, O or NR, and each R group is independently a hydrogen, alkyl, aryl, or heteroaryl.

4. The process according to claim 3, wherein the solvent is used in the form of an aqueous solution in a concentration of not more than 70% by volume.

5. The process according to claim 3, wherein the solvent comprises a polar carbon-oxygen bond.

6. The process according to claim 5, wherein the solvent is used in the form of an aqueous solution in a concentration of not more than 70% by volume.

7. The process of claim 5, wherein the solvent is selected from the group consisting of alkanols and esters.

8. The process according to claim 7, wherein the solvent is used in the form of an aqueous solution in a concentration of not more than 70% by volume.

9. The process of claim 7, wherein the solvent is methanol.

10. The process according to claim 9, wherein the solvent is used in the form of an aqueous solution in a concentration of not more than 70% by volume.

11. The process according to claim 1, wherein the solvent comprises a polar carbon-oxygen bond.

12. The process according to claim 11, wherein the solvent is used in the form of an aqueous solution in a concentration of not more than 70% by volume.

13. The process according to claim 1, wherein the solvent is selected from the group consisting of alkanols and esters.

14. The process according to claim 13, wherein the solvent is used in the form of an aqueous solution in a concentration of not more than 70% by volume.

15. The process according to claim 1, wherein the solvent is methanol.

16. The process according to claim 15, wherein the solvent is used in the form of an aqueous solution in the concentration of not more than 70% by volume.

* * * * *